(12) United States Patent
Chilukuri et al.

(10) Patent No.: US 11,000,831 B2
(45) Date of Patent: May 11, 2021

(54) TRANSITION METAL(S) CATALYST SUPPORTED ON NITROGEN-DOPED MESOPOROUS CARBON AND ITS USE IN CATALYTIC TRANSFER HYDROGENATION REACTIONS

(71) Applicant: Council of Scientific & Industrial Research, New Delhi (IN)

(72) Inventors: Satyanarayana Veera Venkata Chilukuri, Pune (IN); Atul Sopan Nagpure, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 474 days.

(21) Appl. No.: 15/758,804

(22) PCT Filed: Sep. 12, 2016

(86) PCT No.: PCT/IN2016/050304
§ 371 (c)(1),
(2) Date: Mar. 9, 2018

(87) PCT Pub. No.: WO2017/042838
PCT Pub. Date: Mar. 16, 2017

(65) Prior Publication Data
US 2020/0230578 A1 Jul. 23, 2020

(30) Foreign Application Priority Data

Sep. 10, 2015 (IN) .......................... 2833/DEL/2015

(51) Int. Cl.
*B01J 23/46* (2006.01)
*B01J 23/00* (2006.01)
*B01J 35/02* (2006.01)
*B01J 35/10* (2006.01)
*B01J 37/04* (2006.01)
*B01J 37/06* (2006.01)
*B01J 37/34* (2006.01)
*B01J 35/00* (2006.01)
*B01J 21/18* (2006.01)
*C07D 307/36* (2006.01)

(52) U.S. Cl.
CPC .......... *B01J 23/462* (2013.01); *B01J 23/002* (2013.01); *B01J 35/006* (2013.01); *B01J 35/023* (2013.01); *B01J 35/1014* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 37/04* (2013.01); *B01J 37/06* (2013.01); *B01J 37/343* (2013.01); *C07D 307/36* (2013.01); *B01J 21/18* (2013.01)

(58) Field of Classification Search
CPC ... B01J 21/18; B01J 27/24; B01J 23/46; B01J 23/462; B01J 35/006; C07D 307/36
See application file for complete search history.

(56) References Cited

FOREIGN PATENT DOCUMENTS

WO 2017042838 A1 3/2017

OTHER PUBLICATIONS

XU. Journal of the American Chemical Society, 2012, 134, 16987-16990, supporting information pp. S1-S13 (Year: 2012).*
Ayusheev. Applied Catalysis B: Environmental, 2014, 146, 177-185, available online Mar. 18, 2013 (Year: 2013).*
European Patent Office Search Report and Written Opinion dated Feb. 10, 2017 in reference to PCT/IN2016/050304 filed Sep. 12, 2016.
Chuanfang Zhang; "Enhanced Electrochemical Performance of Hydrous RuO2/Mesoporous Carbon Nanocomposites via Nitrogen Doping"; ACS Applied Materials & Interfaces; vol. 6; May 2014; pp. 9751-9759.
Jungho Jae et al.; "Production of Dimethylfuran from Hydroxymethylfurfural through Catalytic Tmasfer Hydrogenation with Ruthenium Supported on Carbon"; ChemSusChem; vol. 6; Jul. 2013; pp. 1158-1162.
Lei Hu et al.; "Selective Transformation of 5-Hydroxymethylfurfural into the Liquid Fuel 2,5-Dimethylfuran over Carbon-Supported Ruthenium"; Industrial & Engineering Chemistry Research; vol. 53; pp. 3056-3064.
Jian Liu, et al.; "Molecular-Based Design and Emerging Applications of Nanoporous Carbon Spheres"; Nature Materials; vol. 14; Aug. 2015; pp. 763-774.
Xuan Xu, et al.; "Synthesis of Palladium Nanoparticles Supported on Mesoporous N-Doped Carbon and Their Catalytic Ability for Biofuel Upgrade"; Journal of the American Chemical Society; vol. 134; Oct. 3, 2012; pp. 16987-16990.
Claudia Antonetti, et al.; "Novel Microwave Synthesis of Ruthenium Nano-particles Supported on Carbon Nanotubes Active in the Selective Hydrogenation of p-chloronitrobenzene to p-chloroaniline"; Applied Catalysis A: General 421-422; 2012; pp. 99-107.
Artemiy Ayusheev, et al.; "Ruthenium Nanoparticles Supported on Nitrogen-Doped Carbon Nanofibers for the Catalytic Wet Air Oxidation of Phenol"; Applied Catalysis B: Environmental ; 2013; pp. 177-185.

(Continued)

*Primary Examiner* — Noble E Jarrell
(74) *Attorney, Agent, or Firm* — Dinsmore & Shohl, LLP

(57) ABSTRACT

The present invention discloses a novel transition metal(s) catalyst supported on nitrogen-doped mesoporous carbon and a process for the preparation of the same. Further, the present invention discloses use of transition metal(s) supported on nitrogen-doped mesoporous carbon catalyst in catalytic transfer hydrogenation reaction. The invention also discloses an improved process for the synthesis of 2,5-Dimethylfuran (DMF) and 2-Methylfuran (MF) from 5-hydroxymethylfurfural (HMF) and furfural respectively, using alcohols as hydrogen donor over a transition metal supported on nitrogen-doped mesoporous carbon, especially ruthenium supported on nitrogen-doped mesoporous carbon without using any co-catalysts.

15 Claims, 6 Drawing Sheets

(56) References Cited

OTHER PUBLICATIONS

Maya Chatterjee, et al.; "Hydrogenation of 5-hydroxymethylfurfural in Supercritical Carbon Dioxide-Water: a Tunable Approach to Dimethylfuran Selectivity"; Green Chemistry; 2014; vol. 16; pp. 1543-1551.

Juan Wang, et al.; "Ruthenium Nanoparticles Supported on Carbon Nanotubes for Selective Hydrogenolysis of Glycerol to Glycols"; Chemistry Letters, vol. 38; No. 6; 2009; pp. 572-573.

Lei Hu, et al.; "Chemoselective Hydrogenation of Biomass-Derived 5-Hydroxymethylfurfural into the Liquid Biofuel 2,5-Dimethylfuran"; Industrial & Engineering Chemistry Research; 2014; vol. 53; 2014; pp. 9969-9978.

Paraskevi Panagiotopoulou, et al.; "Liquid Phase Catalytic Transfer Hydrogenation of Furfural Over a Ru/C Catalyst"; Applied Catalysis A: General; 2014; vol. 480; pp. 17-24.

Thomas B. Rauchfuss, et al.; "Efficient Production of the Liquid Fuel 2,5-Dimethylfuran from Fructose Using Formic Acid as a Reagent"; Biofuels—Angew. Chem. Int. Ed.; 2010; vol. 49; pp. 6616-6618.

Yuriy Roman-Leshkov, et al.; "Production of Dimethylfuran for Liquid Fuels from Biomass-Derived Carbohydrates"; Nature Publishing Group; 2007; vol. 447; pp. 982-986.

Sanchez-Delgado, et al.; "Hydrogenation of arenes and N-heteroaromatic compounds over ruthenium nanoparticles on poly(4-vinylpyridine): a versatile catalyst operating by a substrate-dependent dual site mechanism"; Dalton Transactions; 2011; 40; pp. 10621-10632.

* cited by examiner

TRANSITION METAL(S) CATALYST SUPPORTED ON NITROGEN-DOPED MESOPOROUS CARBON AND ITS USE IN CATALYTIC TRANSFER HYDROGENATION REACTIONS

FIELD OF THE INVENTION

The present invention relates to a novel transition metal(s) supported on nitrogen-doped mesoporous carbon and a process for the preparation of the same. Further, the present invention discloses a use of transition metal(s) supported on nitrogen-doped mesoporous carbon catalyst in catalytic transfer hydrogenation reaction. The invention also discloses an improved process for the synthesis of 2,5-Dimethylfuran (DMF) and 2-Methylfuran (MF) from 5-hydroxymethylfurfural (HMF) and furfural using transition metal(s) supported on nitrogen-doped mesoporous carbon catalyst. More particularly, the present invention also relates to a process for the preparation of 2,5-dimethylfuran (DMF) and 2-methylfuran (MF) from 5-hydroxymethylfurfural (HMF) and furfural, respectively catalyzed by ruthenium (Ru) nanoparticles supported on nitrogen doped mesoporous carbon.

BACKGROUND AND PRIOR ART

In recent years, 2,5-dimethylfuran (DMF), which is produced by the selective hydrogenolysis of biomass-derived 5-hydroxymethylfurfural (HMF) and is considered as a new-fashioned liquid biofuel for transportation, has received much more attention from many researchers in the world. Compared to the current market-leading bioethanol, DMF possesses a higher energy density, a higher boiling point and a higher octane number and is immiscible with water. In view of the diminishing oil reserves and the clear visible signs of climate change attributed to greenhouse gas emissions to the atmosphere, utilization of renewable biomass sources for the production of fuels and chemicals has become imperative. Worldwide, there is a remarkable research activity in this area for the development of processes and catalysts for transforming abundant lignocellulosic biomass into liquid fuels for the transportation sector as well as to prepare platform chemicals. For these efforts to become a commercial reality the developed process has to be economically feasible and the developed catalyst should be cheap and easy to scale-up. Hydrogenolysis reaction holds great promise for the proposed bio-refinery concept, as biomass-derived substrates possess very high oxygen content, which need to be reduced to get useful chemicals and fuels. The selective hydrogenolysis of furfural and 5-hydroxymethylfurfural (HMF) to 2-methylfuran (MF) and 2,5-dimethylfuran (DMF), respectively, holds great potential for the production of liquid fuel substitutes/additives from renewable compounds. Furfural and HMF can be obtained from the acid-catalyzed dehydration of hemicellulose and cellulose-derived carbohydrates, respectively. Both DMF and MF have desirable chemical and physical properties to be used as transportation fuels; with nearly 40% more energy density (35 MJkg$^{-1}$, 31.2 MJkg$^{-1}$) than ethanol. They also have high research octane numbers (RON=119, RON=131), very little solubility in water (2.3 gL$^{-1}$, 7.0 gL$^{-1}$) and ideal boiling points (92-94° C., 64.7° C.). Furthermore, DMF consumes only one-third of the energy for the separation by distillation, compared to that required for the separation of ethanol from fermented broth. The DMF and MF have been successfully tested as biofuels in a single cylinder spray guided direct-injection spark-ignition engine. Their performance was satisfactory against gasoline in terms of ignition, emission and combustion properties. These excellent characteristics make DMF and MF as promising renewable fuels for transportation.

One of the vital challenges for the upgradation of HMF and furfural to value added chemicals and fuels is the product selectivity. For instance, hydrogenation of HMF and furfural results in a mixture of ring- and side chain-hydrogenated products along with ring-opening products. Decoupling these processes is highly important for using furans as renewable fuels. The hydrogenolysis of HMF and furfural into DMF and MF, respectively, were studied over various supported metal catalysts by using molecular hydrogen. The break-through of preparing DMF from biomass-derived compound (HMF) was first reported by Roman-Leshkov et al. using a bimetallic CuRu/C catalyst with 71% DMF yield at 220° C. and 6.8 bar $H_2$ pressure. Chatterjee et al. reported the use of Pd/C catalyst in supercritical $CO_2$ to get high yield of DMF. But, this process involves the use of high pressure $CO_2$ and $H_2$.

Article titled "Chemoselective Hydrogenation of Biomass-Derived 5-Hydroxymethylfurfural into the Liquid Biofuel 2,5-Dimethylfuran" by L Hu et al. published in Ind. Eng. Chem. Res., 2014, 53 (24), pp 9969-9978 reports catalytic systems and the latest research achievements for the selective hydrogenation of HMF into DMF in light of the diversity of hydrogen donors such as molecular hydrogen, formic acid, alcohols, and water are systematically summarized and discussed. The study shows the maximum yield of DMF up to 94.6% and 100% conversion of HMF by using Ru/C as catalyst in presence of THF solvent and molecular hydrogen.

Article titled "Selective Transformation of 5-Hydroxymethylfurfural into the Liquid Fuel 2,5-Dimethylfuran over Carbon-Supported Ruthenium' by L Hu et al. published in Ind. Eng. Chem. Res., 2014, 53 (8), pp 3056-3064 reports a simple and efficient process for the selective hydrogenation of 5-hydroxymethylfurfural (HMF) into the high-quality liquid fuel 2,5-dimethylfuran (DMF) in the presence of tetrahydrofuran (THF) using carbon-supported ruthenium (Ru/C) which led to 94.7% DMF yield with 100% HMF conversion at a relatively mild reaction temperature of 200° C. for only 2 h.

Article titled "Effect of hydrogen donor on liquid phase catalytic transfer hydrogenation of furfural over a Ru/RuO$_2$/C catalyst" by P Panagiotopoulou et al. published in Applied Catalysis A: General, 2014, 480, pp 17-24 reports catalytic transfer hydrogenation of furfural toward methyl furan over a Ru/C catalyst in the temperature range of 120-200° C. using 2-propanol as a solvent. An optimum methyl furan yield of 61% has been achieved using said process as reported.

Article titled "Production of Dimethylfuran from Hydroxymethyl-furfural through Catalytic Transfer Hydrogenation with Ruthenium Supported on Carbon" by J Jae et al. published in ChemSusChem, 2013, 6(7), pp 1158-62 reports transfer hydrogenation using alcohols as hydrogen donors and supported ruthenium catalysts results in the selective conversion of hydroxymethylfurfural to dimethylfuran (>80% yield).

Article titled "Novel microwave synthesis of ruthenium nanoparticles supported on carbon nanotubes active in the selective hydrogenation of p-chloronitrobenzene to p-chloroaniline" by C Antonetti et al. published in Applied Catalysis A: General, 2012, 421-422, pp 99-107 reports selective hydrogenation of p-chloronitrobenzene (p-CNB) to p-chloroaniline (p-CAN) using carbon nanotubes (CNTs) supported ruthenium nanoparticles with almost complete substrate conversion with total selectivity to the target product.

Article titled "Ruthenium nanoparticles supported on nitrogen-doped carbon nanofibers for the catalytic wet air oxidation of phenol" by AB Ayusheev et al. published in Applied Catalysis B: Environmental, 2014, Volume 146, pp 177-185 reports effect of nitrogen content in N-doped carbon nanofibers (N-CNFs) on the catalytic activity of Ru/N-CNFs in the wet air oxidation of phenol. In the case of Ru-containing catalysts, nitrogen in N-CNFs was found to be responsible for both the increased activity and stability of the catalysts toward deactivation. The Ru/N-CNFs catalyst is prepared by using wetness impregnation technique.

Article titled "Ruthenium Nanoparticles Supported on Carbon Nanotubes for Selective Hydrogenolysis of Glycerol to Glycols" by J Wang et al. published in Chemistry Letters, 2009, 38(6), pp 572-573 reports Ru nanoparticles supported on carbon nanotubes showed efficient reactivity for hydrogenolysis of aqueous glycerol solution to produce glycols of 1,2-propanediol and ethylene glycol. The glycerol conversion along with the product selectivity depended essentially on the mean size of Ru nanoparticles.

Most of the reported processes for the hydrogenolysis of HMF to DMF and furfural to MF were conducted under high-pressure $H_2$ and at elevated reaction temperatures. Such type of processes are energy intensive, thus difficult to commercialize. It is desirable to minimize the use of external $H_2$ required for biofuel production, especially if this $H_2$ has to be prepared from fossil fuels. The catalytic transfer hydrogenation (CTH) process for reducing the substrates has advantages compared to processes involving molecular $H_2$. Several investigators employed CTH process for the conversion of HMF to DMF and furfural to MF over various metal catalysts. Instead of molecular $H_2$, secondary alcohols, supercritical methanol, cyclohexane or 1,4-butanediol were used as a hydrogen source as well as reaction media. Rauchfuss et al. reported DMF yield up to 95% using Pd/C as catalyst and formic acid as a hydrogen donor. However, this process needs simultaneous use of formic acid and $H_2SO_4$ to get high yield of DMF. Use of acids is not environment friendly and also requires corrosion-resistant equipment for the process that will add cost to the process. Moreover, the reported CTH processes include the use of mineral acids as co-catalysts to improve the hydrogenation activity, which are difficult to separate from the reaction mixture and are responsible for undesirable side reactions.

Therefore, there is need to develop an environment friendly alternative process for the hydrogenolysis of HMF to DMF and furfural to MF by CTH. Accordingly, the present inventors developed an improved process for hydrogenolysis of HMF to DMF and furfural to MF using alcohols as hydrogen donor instead of molecular $H_2$ over a Ru supported on nitrogen-doped mesoporous carbon without using any co-catalysts.

OBJECT OF THE INVENTION

The main object of the present invention is to develop a novel transition metal(s) catalyst supported on nitrogen-doped mesoporous carbon. The another object of the present invention to provide a process for the preparation of the same. Further, object the present invention is use of transition metal(s) catalyst supported on nitrogen-doped mesoporous carbon in catalytic transfer hydrogenation reaction. Yet another object of the invention is to provide an improved process for the synthesis of 2,5-Dimethylfuran (DMF) and 2-Methylfuran (MF) from 5-hydroxymethylfurfural (HMF) and furfural using transition metal(s) catalyst supported on nitrogen-doped mesoporous carbon.

SUMMARY OF THE INVENTION

Accordingly present invention provides a catalyst composition comprising;

a transition metal supported on nitrogen doped mesoporous carbon; wherein the transition metal(s) in the range of 0.5 to 10 weight % of the catalyst.

In another embodiment the transition metal(s) of the catalyst is selected from the group consisting of Ru, Pt, Pd, Rh, Au, Ag, Os, Ir, Cu, Ni, Re, Cr, Mn, Fe, Zn, Co; either alone or in combination of any two or more metals In another embodiment the BET surface area of the transition metal(s) catalyst in the range of 30 to 1200 $m^2/g$.

In another embodiment the BET surface area of the transition metal(s) catalyst in the range of 36 to 1000 $m^2/g$.

In another embodiment the total pore volume of the transition metal(s) catalyst in the range of 0.07 to 1.2 cc/g.

In another embodiment the average particle/crystal size of the transition metal(s) in the range of 1 to 10 nm.

In another embodiment the present invention provides a process for synthesis of metal(s)-nitrogen doped mesoporous carbon catalyst comprising the steps of;

a. dispersing nitrogen doped mesoporous carbon in deionized water under ultrasonication to obtain high dispersion, b. charging transition metal chloride to above dispersion obtained in step (a) under ultra sonication and stirring the mixture at 70-90° C. for 6 to 12 hours.

c. cooling the mixture of step (b) and charging aqueous solution of $NaBH_4$ slowly under ultrasonication and stirring for 30-60 minutes.

d. filtering the solution and washing with deionized water and drying at 80-100° C. for 10-12 hours to obtain the catalyst.

In another embodiment the transition metal chloride selected from the chlorides of Ru, Pt, Pd, Rh, Au, Ag, Os, Ir, Cu, Ni, Re, Cr, Mn, Fe, Zn, Co; either alone or in combination of any two or more metal chlorides.

In another embodiment, the present invention provides a process for the preparation of 2,5-Dimethylfuran (DMF) and 2-Methylfuran (MF) from 5-Hydroxymethylfurfural (HMF) and furfural using alcohols as hydrogen donor instead of molecular $H_2$ over transition metal supported on nitrogen-doped mesoporous carbon, especially Ru supported on nitrogen-doped mesoporous carbon without using any co-catalysts.

In another embodiment the transition metal supported on nitrogen-doped mesoporous carbon used is Ru supported on nitrogen-doped mesoporous carbon for the preparation of 2,5-Dimethylfuran (DMF) and 2-Methylfuran (MF) from 5-Hydroxymethylfurfural (HMF) and furfural In another embodiment the catalytic transfer hydrogenation (CTH) agents are selected from alcohols, organic acids or organic acid salts or mixture thereof.

In another embodiment the alcohol used as catalytic transfer hydrogenation (CTH) agents is selected from the group consisting of 2-propanol, 2-butanol, methanol, ethanol, 1-propanol.

In another embodiment the organic acid used as catalytic transfer hydrogenation (CTH) agents is selected from the group consisting formic acid, acetic acid, propionic acid and butyric acid etc In another embodiment the catalytic transfer hydrogenation reaction is carried out in the presence of molecular hydrogen alone or along with catalytic transfer hydrogenation agent.

In another embodiment the temperature of the catalytic transfer hydrogenation reaction is in the range of 80-170° C.

In preferred embodiment, the nitrogen content in said transition metal catalyst support is 3-15 wt %.

In preferred embodiment, the metal content in said ruthenium catalyst in the range of 0.5 to 10 weight % of the catalyst In preferred embodiment, the nitrogen content in said ruthenium catalyst support is 3-15 wt %.

In another preferred embodiment, the yield of 2,5-Dimethylfuran (DMF) is greater than 80% and conversion of 5-hydroxymethylfurfural (HMF) is 100% in catalytic transfer hydrogenation reaction.

In another preferred embodiment, the yield of 2,5-Dimethylfuran (DMF) is greater than 80% and conversion of 5-hydroxymethylfurfural (HMF) is 100% when ruthenium metal nitrogen doped mesoporous carbon used as catalyst.

In still another preferred embodiment, the yield of 2-methylfuran (MF) is >87% and conversion of furfural is 100% in catalytic transfer hydrogenation reaction.

In still another preferred embodiment, the yield of 2-methylfuran (MF) is >87% and conversion of furfural is 100% when ruthenium metal nitrogen doped mesoporous carbon used as catalyst.

DETAILED DESCRIPTION OF THE INVENTION

The invention will now be described in detail in connection with certain preferred and optional embodiments, so that various aspects thereof may be more fully understood and appreciated.

In view of the above, the present invention provides a process for the preparation of 2,5-dimethylfuran (DMF) and 2-methylfuran (MF) from 5-hydroxymethylfurfural (HMF) and furfural, respectively using alcohols as hydrogen donor instead of molecular $H_2$ over Ru supported on nitrogen-doped mesoporous carbon without using any co-catalysts.

In an embodiment, the present invention provides an improved process for the synthesis of 2,5-dimethylfuran (DMF) and 2-methylfuran (MF) from 5-hydroxymethylfurfural (HMF) and furfural, respectively catalyzed by transition metal nanoparticles supported on nitrogen doped mesoporous carbon in the presence of 2-propanol as hydrogen donor in the temperature range of 80-170° C., in that nitrogen content in said catalyst is in the range of 3-15 wt %.

In preferred embodiment, the yield of 2,5-Dimethylfuran (DMF) is greater than 80% and conversion of 5-hydroxymethylfurfural (HMF) is 100%.

In another preferred embodiment, the yield of 2-methylfuran (MF) is >87% and conversion of furfural is 100%.

In still another preferred embodiment, said reaction is carried out at temperature range in the range of 80-170° C.

The ruthenium content in said catalyst is in the range of 1-10 wt %. Preferably the ruthenium content in said catalyst is 2 wt %.

In one embodiment, the transition metals are selected from Ru, Pt, Pd, Rh, Au, Ag, Os, Ir, Cu, Ni, Re, Cr, Mn, Fe, Zn, Co; either alone or in combination of any two or more metals in the range of 0.5-10 wt % of the catalyst.

Figure 1:
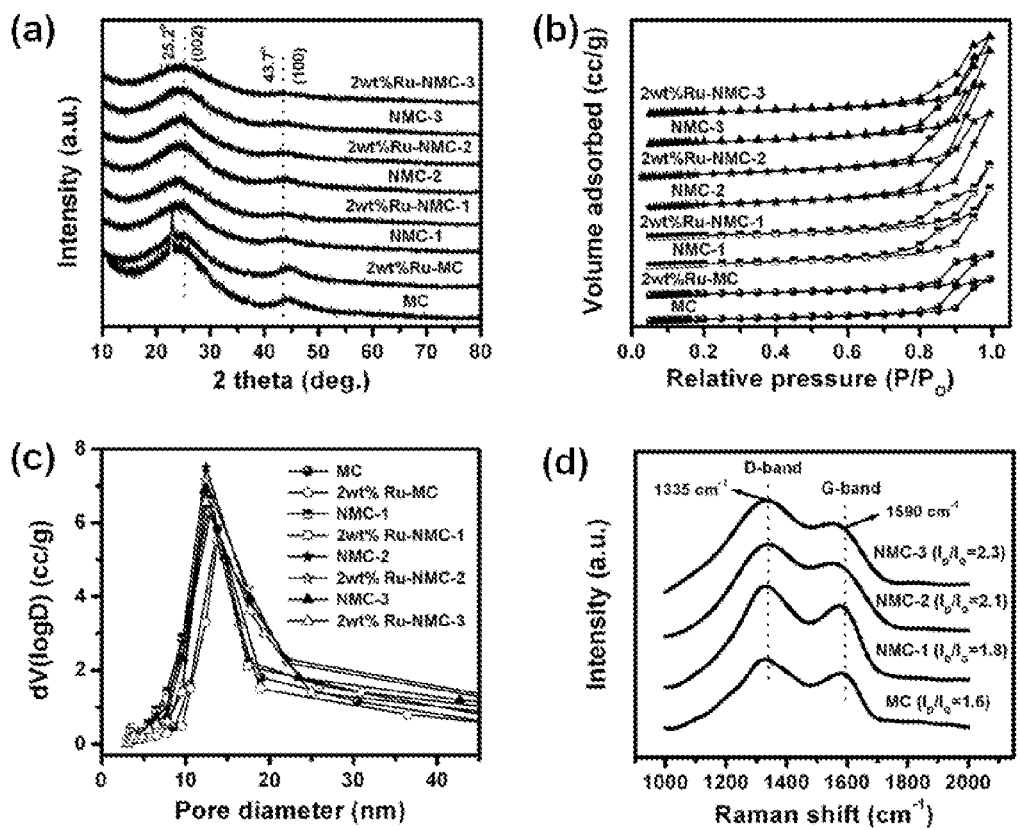
FIG. 1: (a) XRD, (b) $N_2$ adsorption-desorption isotherm, (c) BJH pore size distribution and (d) Raman spectra of the various samples.

The NMCs are prepared by a colloidal silica nanocasting route, which involved the mixing of melamine-phenol-formaldehyde polymer sol with colloidal silica nanoparticles to obtain composite hydrogel. Its subsequent carbonization in $N_2$ atmosphere at 800° C. followed by silica dissolution by treatment with NaOH, gave NMCs with disordered mesopores (Table 1). The X-ray diffraction (XRD) patterns of nitrogen-free carbon (MC), nitrogen-doped carbon samples (NMC-1, NMC-2 and NMC-3) and as-synthesized 2 wt % Ru deposited on various supports are shown in FIG. 1a. The formation of highly dispersed Ru nanoparticles is proven by XRD (FIG. 1a), as no diffraction peaks pertaining to metallic Ru are observed. Moreover, no change in diffraction peaks of the supports on Ru loading is observed, indicating that the Ru loading has no effect on the structure of the supports.

As shown in FIG. 1b, support materials and Ru containing samples shows similar type IV adsorption-desorption isotherms with $H_2$ hysteresis loop, corresponding to the typical mesoporous structure of the materials. These results suggest that variation in nitrogen content does not strongly affect the mesoporous structure of the samples. Their BJH pore size distributions are similar in the range of 10-20 nm (FIG. 1c).

The formation of graphitic ordered carbon is further proved by Raman spectroscopy (FIG. 1d). Raman spectra show characteristic D- and G-bands of disordered graphitic carbon at 1335 and 1590 cm$^{-1}$ respectively. The intensity ratios of the D-band to the G-band ($I_D/I_G$, calculated from integral area of the peaks) are 1.6, 1.8, 2.1 and 2.3 for MC, NMC-1, NMC-2 and NMC-3, respectively. These results show that the defects in graphite-like layers enhanced with increasing nitrogen content.

Figure 2:
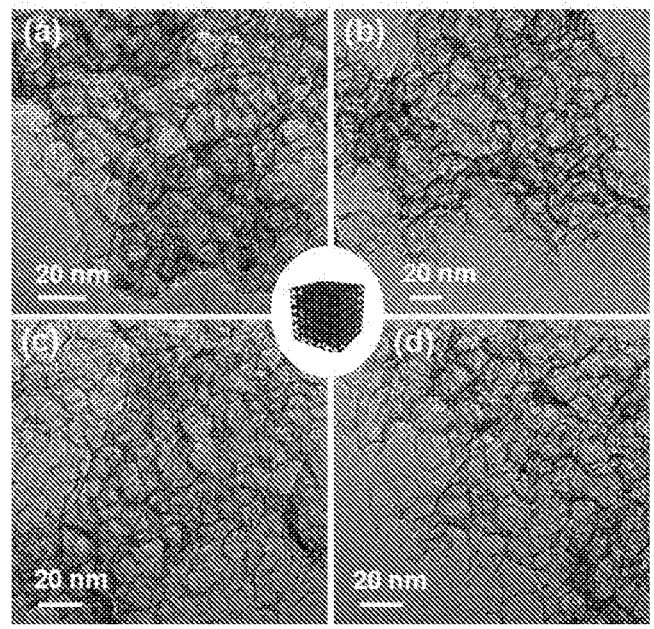
FIG. 2: TEM image of the (a) MC, (b) NMC-1, (c) NMC-2 and (d) NMC-3.
Figure 3:
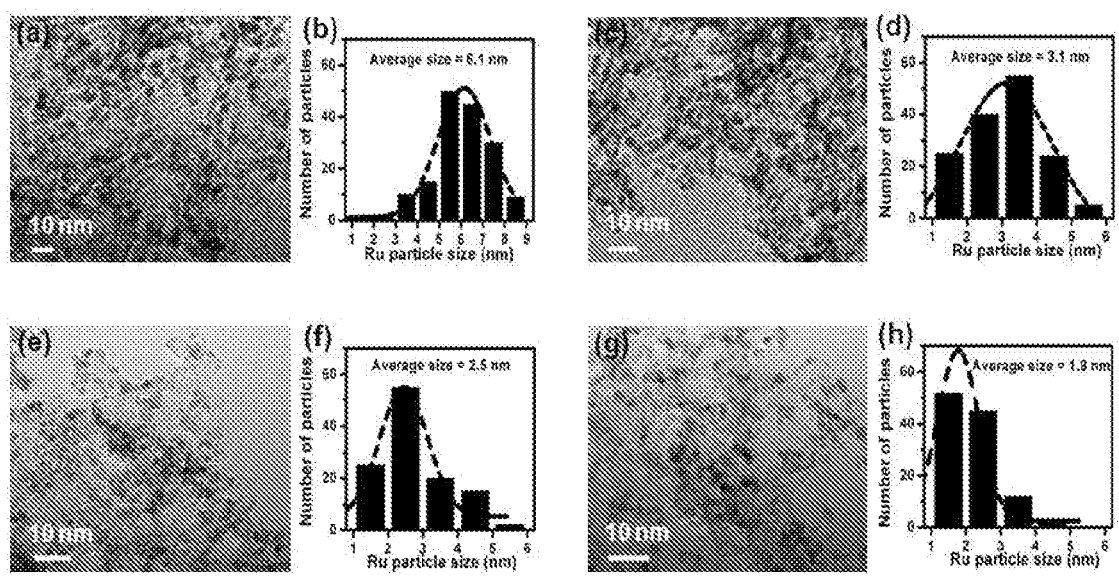
FIG. 3: TEM images and the Ru nanoparticles size distribution for 2 wt % Ru-MC (3a and 3b), 2 wt % Ru-NMC-1 (3c and 3d), 2 wt % Ru-NMC-2 (3e and 3f) and 2 wt % Ru-NMC-3 (3g and 3h), respectively.

The mesoporous structure of the MC and nitrogen-doped carbon samples is further confirmed by transmission electron microscopy (TEM) observations (FIG. 2). From TEM images, nitrogen containing samples (FIGS. 2b, 2c and 2d) have no differences when compared with their nitrogen-free counterpart (FIG. 2a), consisting of spherical mesopores with a disordered amorphous carbon structure. The Ru nanoparticles sizes as well as their distribution for various Ru containing catalysts are investigated by TEM (FIG. 3). The TEM results suggested that the dominant contributor for stabilizing Ru nanoparticles is the nitrogen doped in the carbon structure and increasing nitrogen content in the sample led to decrease in the size of Ru nanoparticles.

Figure 4:
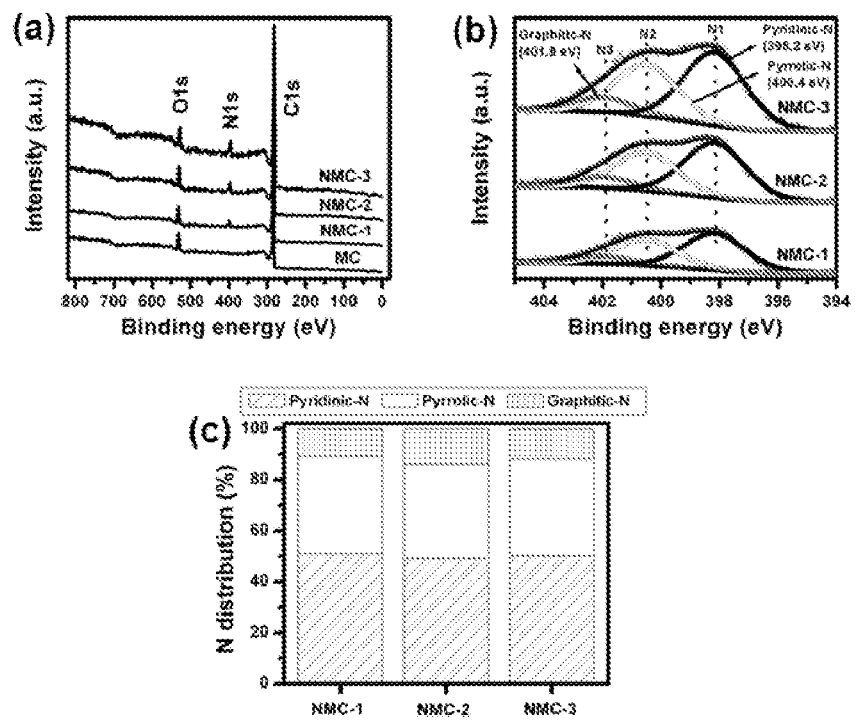
FIG. 4: (a) XPS survey and (b) high-resolution N is spectra of the NMCs. (c) The distribution of N species in the NMCs from resolving peaks of the N 1s spectra.

The X-ray photoelectron spectroscopy (XPS) is employed to investigate the nitrogen-carbon bonds formed in the carbon framework. In XPS only oxygen, carbon and nitrogen are detected in the overall region scanned (FIG. 4a). XPS of C is shows very similar peak at 284.6 eV, which is associated with the graphitic carbon, suggesting that most of the C atoms are assembled in conjugated honeycomb lattices.

Figure 5:
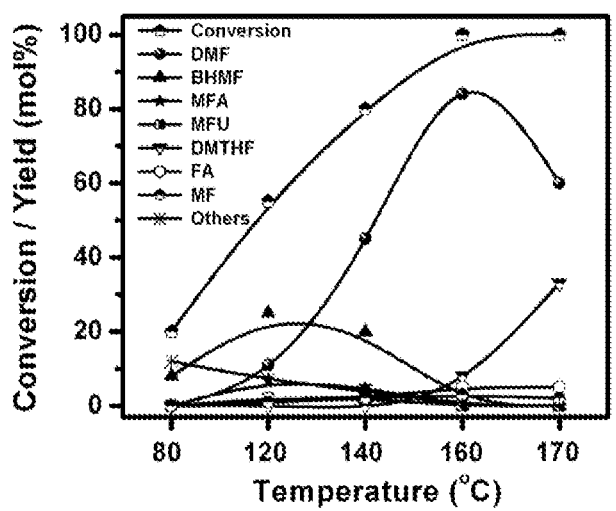
FIG. 5: Effect of reaction temperature on HMF conversion and product yields. Reaction conditions: HMF (1 mmol); catalyst (2 wt % Ru-NMC-3, 25 mg); $N_2$ pressure (20 bar); solvent and hydrogen donor (2-propanol, 25 mL); time (8 h). Other products include ethers.

The catalyst evaluation for hydrogenolysis of HMF to get DMF is performed using 2-propanol as a hydrogen donor in a batch reactor. FIG. 5 shows HMF conversion and product distributions as a function of reaction temperature over 2 wt % Ru-NMC-3 catalyst. The catalytic transfer hydrogenation (CTH) reaction occurs at a lower reaction temperature (80° C.) and DMF yield increased with increasing temperature. At lower temperature, the primary product is 2,5-bis(hydroxymethyl)furan (BHMF) and upon increasing the temperature to 160° C., BHMF is completely converted to DMF with a yield up to 84 mol % at 100 mol % HMF conversion after 8 h of reaction. Other products observed at 120 and 140° C. are hydrogenated furans: 5-methyl furfural (MFU), 5-methyl furfuryl alcohol (MFA), 2-methylfuran (MF) and furfuryl alcohol (FA). The formation of FA indicates the occurrence of decarbonylation reaction, however, the yield of FA is low (<4 mol %). The formation of MFU suggested that hydrogenolysis of —OH group in HMF occur in parallel to the hydrogenation of the —CHO group. In addition, ethers are also observed at lower temperature (80 and 120° C.), which are formed via etherification of BHMF or MFA and 2-propanol. They are not observed upon increasing the reaction temperature (160 and 170° C.).

Figure 6:
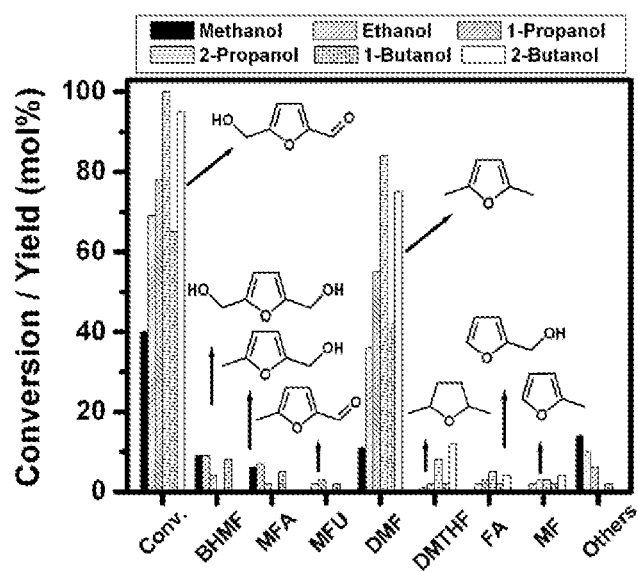
FIG. 6: Effect of hydrogen donor on HMF conversion and product yields. Reaction conditions: HMF (1 mmol); catalyst (2 wt % Ru-NMC-3, 25 mg); temperature (160° C.); $N_2$ pressure (20 bar); solvent and hydrogen donor (25 mL); time (8 h). Other products include ethers.

The effect of hydrogen donor on HMF conversion and product yields is investigated at 160° C. over 2 wt % Ru-NMC-3 catalyst. The results (FIG. 6) clearly indicate that the activity of catalyst heavily depends on the type of alcohol used. The HMF conversion increased from 40 to 100 mol % and the following reactivity order is observed: methanol<1-butanol<ethanol<1-propanol<2-butanol<2-propanol. Among the hydrogen donors tested, 2-propanol showed highest activity giving 84 mol % DMF yield. The formation of ethers is negligible in 2-propanol and 2-butanol but significant in other alcohols (2-14 mol %). This shows that etherification reaction favored with lower chain alcohols (methanol, ethanol and 1-propanol) indicative of steric effect.

In preferred embodiment, 2-propanol is used as hydrogen donor.

In order to investigate the effect of nitrogen content of the catalyst on CTH activity, the Ru catalyst supported on various nitrogen containing mesoporous carbons and nitrogen-free carbon are tested for HMF hydrogenolysis (Table 3). The HMF conversions are 41, 61, 79 and 100 mol % with DMF yield of 11, 30, 55 and 84 mol % on 2 wt % Ru-MC, 2 wt % Ru-NMC-1, 2 wt % Ru-NMC-2 and 2 wt % Ru-NMC-3 catalysts, respectively, which shows that the catalytic activity is improved with increasing nitrogen content in the catalyst. The high nitrogen content in NMC-3 not only led to very stable and homogeneous dispersion of Ru nanoparticles but also enriches the electron density of the Ru nanoparticles, which accelerates the hydrogenolysis reaction, as compared to nitrogen-free catalyst (2 wt % Ru-MC). The results also shows that the nitrogen plays a key role in the dehydrogenation of 2-propanol leading to higher $H_2$ pressure.

In preferred embodiment, nitrogen content in said catalyst is 3-15 wt %.

It is possible that adsorbed hydrogen species formed by the dehydrogenation of 2-propanol during CTH process can directly hydrogenate HMF molecule adsorbed on Ru nanoparticles instead of being released as $H_2$. To understand this aspect, HMF hydrogenation is performed at $H_2$ pressure of 7 bar (total pressure developed including $H_2$ partial pressure during CTH reaction at 160° C. over 2 wt % Ru-NMC-3 with 2-propanol) using tetrahydrofuran (THF) as solvent. The results shows HMF conversion and DMF yield were 86 and 59 mol %, respectively, which are inferior to those using 2-propanol as hydrogen donor (compare entry 5 and 7 in Table 3). This result strongly suggests that HMF hydrogenation using hydrogen donors can be more efficient than that using external $H_2$ gas.

The 2 wt % Ru-NMC-3 catalyst is compared with 2 wt % Ru-AC under the same reaction conditions as well as with other oxide-supported Ru nanoparticles, including 2 wt % Ru-CeO$_2$, 2 wt % Ru—MgO, 2 wt % Ru-TiO$_2$, 2 wt % Ru—Mg(Al)O and 2 wt % Ru-γ-Al$_2$O$_3$. Catalyst 2 wt % Ru-NMC-3 showed remarkably high activity in CTH, giving 100 mol % HMF conversion and 84 mol % DMF yield (Table 4). Oxide and AC supported Ru nanoparticles were not effective for this reaction, affording lower yields of DMF than 2 wt % Ru-NMC-3. In case of 2 wt % Ru-γ-Al$_2$O$_3$ and 2 wt % Ru—TiO$_2$, the main product was BHMF (entry 6 and 7, Table 4). These results show that these two catalysts have ability towards carbonyl group hydrogenation to hydroxyl group, but have less ability for C—O bond hydrogenolysis. From these results, it is clear that the nature of the support plays an important role in the activity and selectivity of Ru based catalysts in CTH reactions.

The CTH of HMF is investigated using NMC-3 supported Ru, Pt, Pd, Rh, Ni, Cu and Au catalysts. The HMF conversion varied in the range of 21 to 100 mol % and followed the reactivity order of Cu<Ni<Au<Rh<Pt<Pd=Ru (Table 5). Gratifyingly, an excellent DMF yield of 84 mol % with 100 mol % HMF conversion was obtained over Ru-based catalyst (Table 5, entry 1). Interestingly, when the reaction was conducted with Pd catalyst, significant amount of decarbonylation product FA was obtained (Table 5, entry 3), indicating Pd is more suitable for HMF decarbonylation.

Figure 7:
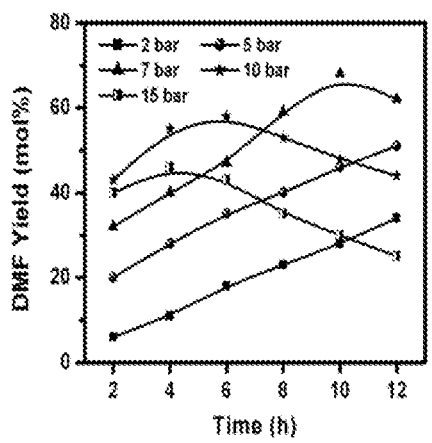
FIG. 7: Effect of $H_2$ pressure on DMF yields over 2 wt % Ru-NMC-3 as a function of reaction time. Reaction conditions: HMF (1 mmol); catalyst (25 mg); temperature (160° C.); solvent (THF, 25 mL).

The effect of $H_2$ pressure on the DMF yields is studied by varying the pressure from 2-15 bar at 160° C. in THF solvent over 2 wt % Ru-NMC-3 catalyst (FIG. 7). When the reaction was carried out at low pressure (2 and 5 bar), the intermediate products such as BHMF and MFA formed in significant quantities, which may be converted to DMF on prolonging the reaction time. On further increasing $H_2$ pressure (7 bar);

the DMF yield reaches the maximum (68 mol %) and the yield decreased on continuation of the reaction for further duration. This decrease in DMF yield is due to its ring hydrogenation, leading to the formation of 2,5-dimethyltetrahydrofuran (DMTHF). Increasing $H_2$ pressure further to 10 and 15 bar, has an adverse effect on the DMF yield. At higher $H_2$ pressure, DMF yield suppressed mostly due to the increased rate of consecutive ring hydrogenation of DMF, led to the formation of DMTHF in significant amounts. Moreover, the concentration of other undesirable by-products such as 5-methyl tetrahydrofurfuryl alcohol (MTHFA), 2,5-bis(hydroxymethyl)tetrahydrofuran (BHMTHF) and hexanediol increased at higher $H_2$ pressure.

Figure 8:
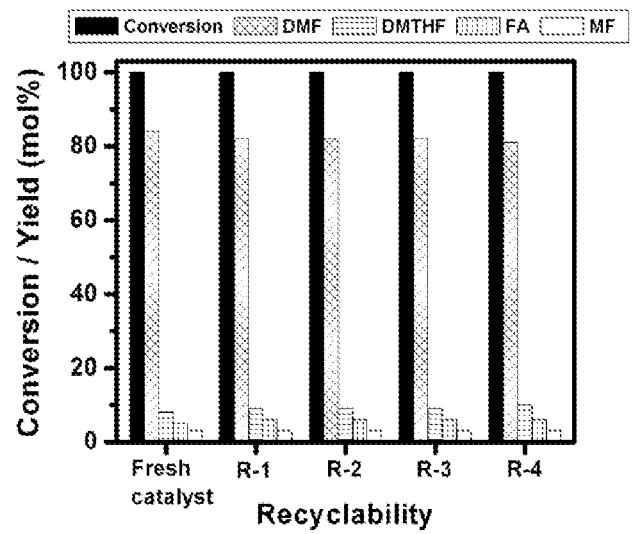
FIG. 8: Recyclability study in CTH of HMF to DMF over 2 wt % Ru-NMC-3. Reaction conditions: molar ratio of HMF to Ru (200); temperature (160° C.); $N_2$ pressure (20 bar); solvent and hydrogen donor (2-propanol, 25 mL); time (8 h).

The recyclability of the 2 wt % Ru-NMC-3 catalyst is evaluated by repeating the reaction with the same catalyst (FIG. 8). The results show that the catalytic performance remains same even after being reused for four times. These results indicate good stability of the catalyst. ICP-OES analysis showed no leaching of Ru after each recycle. Moreover, the amount of Ru in the catalyst after four cycles is found to be similar to that of starting catalyst.

Figure 9:
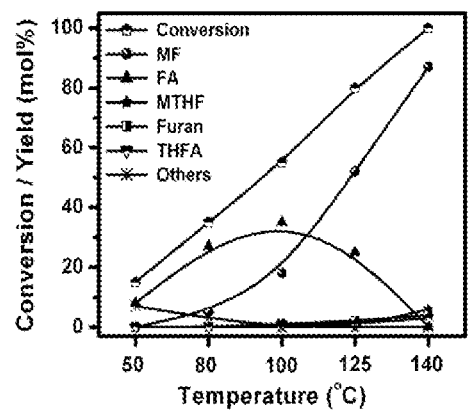
FIG. 9: Effect of reaction temperature on furfural conversion and product yields. Reaction conditions: furfural (5 mmol); catalyst (2 wt % Ru-NMC-3, 25 mg); $N_2$ pressure (20 bar); solvent and hydrogen donor (2-propanol, 25 mL); time (10 h). Others include ethers.

The 2 wt % Ru-NMC-3 catalyst was also investigated for hydrogenolysis of furfural to get 2-methylfuran (MF). The effect of temperature on the furfural conversion and product yields over 2 wt % Ru-NMC-3 catalyst is investigated by varying the reaction temperature in the range of 50-140° C. (FIG. 9). The primary product of the transfer hydrogenation of furfural is FA, which is prominent at lower temperature (80, 100 and 125° C.). In a consecutive step, hydrogenolysis of the —OH group in FA yields MF up to 87 mol % at 140° C. In parallel to hydrogenation, furfural also undergoes decarbonylation reaction to furan. Furthermore, furan-ring hydrogenated products like 2-methyl tetrahydrofuran (MTHF) and tetrahydrofurfuryl alcohol (THFA) have also been observed.

Figure 10:
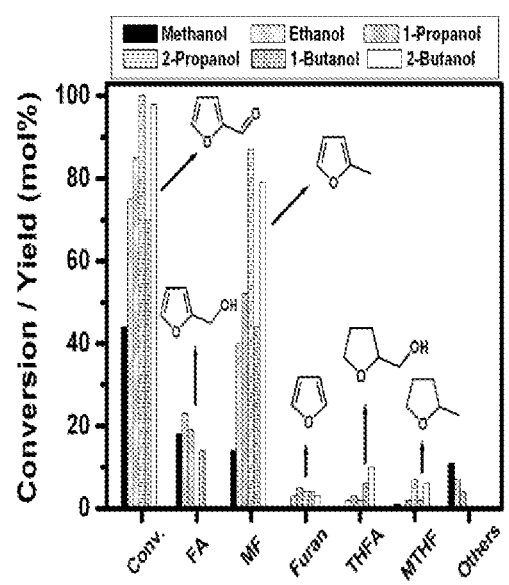
FIG. 10: Effect of hydrogen donor on furfural conversion and product yields. Reaction conditions: furfural (5 mmol); catalyst (2 wt % Ru-NMC-3, 25 mg); $N_2$ pressure (20 bar); solvent and hydrogen donor (25 mL); time (10 h). Others include ethers.

The effect of hydrogen donor on furfural conversion and product yields is investigated at 140° C. over 2 wt % Ru-NMC-3 catalyst (FIG. 10). The results clearly suggested that the catalyst activity is greatly depends on the nature of hydrogen donor. The furfural conversion increased from 44 to 100 mol % and follows the reactivity order: methanol<1-butanol<ethanol<1-propanol<2-butanol<2-propanol. Among the hydrogen donors tested, 2-propanol displayed the highest activity leading to 87 mol % MF yield. These results are in good agreement with the reported results, which normally reports that in CTH secondary alcohols have a better tendency to release hydrogen than primary alcohols.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of Nitrogen-Doped Mesoporous Carbons (NMC)

The NMCs were prepared by colloidal silica assisted sol-gel process, using melamine as a nitrogen source. In a typical synthetic procedure, 3.67 g of phenol (39 mmol) and 6.33 g of formaldehyde (78 mmol) were added drop-wise to 50 mL of NaOH solution (0.2 M, 10 mmol) under stirring. This mixture was stirred at room temperature for 20 min and then heated in an oil bath at 70° C. while stirring, for 40 minutes. About 4.92 g of melamine (39 mmol) and another part of formaldehyde (9.5 g, 107 mmol) were then added to the above solution with continuous stirring for 30 min. This was followed by the addition of 50 g of Ludox SM-30 sol (30 wt % $SiO_2$) with stirring for 1 h. The suspension was then transferred to sealed bottle and heated at 80° C. for 3 days. The obtained gels were dried at 80° C. and powdered using mortar-pestle. The material obtained was carbonized in nitrogen flow at 800° C. for 3 h while raising the temperature at a heating rate of 5° C./min. The NMC was obtained after dissolution of the silica in 2M NaOH solution at 80° C. for 12 h. The solid obtained was washed with distilled water until pH is close to neutral and dried at 100° C. for 10 h. The NMCs with different nitrogen contents were prepared by changing the mole ratio of melamine to phenol. The nitrogen free mesoporous carbon (MC) was also prepared by using above process without adding any melamine content.

Example 2: Synthesis of Ru-NMC

The catalyst 2 wt % Ru-NMC was synthesized by modified ultrasonic-assisted method. Typically, 0.1 g of NMC was dispersed in 50 mL of deionized water in a 100 mL round bottom flask by ultrasonication (20 min). To it, 0.5 mL of aqueous solution of $RuCl_3$ (Ru content 4 mg/mL) was added under agitation in ultrasonicator. This mixture was stirred at 80° C. for 6 h and cooled to room temperature. Then, aqueous solution of $NaBH_4$ (Ru/$NaBH_4$=1:4 mol $mol^{-1}$) was added to it slowly under ultrasonication (30 min). The solution was filtered and washed with deionized water. The resulting 2 wt % Ru-NMC catalyst was dried at 80° C. for 10 h and used as catalyst for hydrogenolysis reactions. Catalyst samples with different Ru loadings (0.5, 1 and 5 wt %) were prepared using a similar procedure by taking appropriate amounts of $RuCl_3$. Catalysts 2 wt % Ru-MC, 2 wt % Ru-AC (AC-activated carbon), 2 wt % Pd-NMC, 2 wt % Pt-NMC, 2 wt % Rh-NMC, 5 wt % Ni-NMC, 5 wt % Cu-NMC and 2 wt % Au-NMC were also prepared by adopting above procedure.

Example 3: Hydrogenolysis of HMF or Furfural

All the reactions were carried out using 100 mL Parr autoclave (SS316). In a typical experiment, the reactor was charged with 1 mmol HMF (or 5 mmol furfural), hydrogen donor (25 mL), n-decane (0.2 g, internal standard) and required amount of freshly prepared catalyst. The reactor contents were mixed thoroughly and the reactor was sealed, purged 2-3 times with $N_2$ and pressurized to 20 bar $N_2$ pressure. Subsequently, the reaction vessel was heated under stirring at required temperature for a desired duration. Liquid samples were withdrawn periodically during the reaction and analyzed by GC (Agilent 7890A) equipped with a flame ionization detector (FID) having CP Sil 8CB capillary column (30 m length, 0.25 mm diameter). Product identification was done using authentic standards and GC-MS (Varian, Saturn 2200) analysis.

Example 4: Characterization of Catalysts

The NMCs were prepared by a colloidal silica nanocasting route, which involved the mixing of melamine-phenol-formaldehyde polymer sol with colloidal silica nanoparticles to obtain composite hydrogel. Its subsequent carbonization in $N_2$ atmosphere at 800° C. followed by silica dissolution by treatment with NaOH, gave NMCs with disordered mesopores (Table 1). The X-ray diffraction (XRD) patterns of nitrogen-free carbon (MC), nitrogen-doped carbon samples (NMC-1, NMC-2 and NMC-3) and as-synthesized 2 wt % Ru deposited on various supports are shown in FIG. 1a. These samples exhibited very similar diffraction features. Broader diffraction peaks are observed at around 25.2 (2θ) and 43.7° (2θ) that correspond to the (002) and (100) planes of graphite, respectively. The (002)-diffraction peak gradually broadens with the increasing nitrogen content in the sample. The intensity of (100)-diffraction peak related to interlayer organization gradually decreases with increasing nitrogen content and even disappears when nitrogen content reaches 11.6 wt % (NMC-3). However, the positions of two peaks (25.2 and 43.7°) do not change with the nitrogen content. The formation of highly dispersed Ru nanoparticles was proven by XRD (FIG. 1a), as no diffraction peaks pertaining to metallic Ru were observed. Moreover, no change in diffraction peaks of the supports on Ru loading was observed, indicating that the Ru loading has no effect on the structure of the supports. As shown in FIG. 1b, support materials and Ru containing samples shows similar type IV adsorption-desorption isotherms with an H2 hysteresis loop, corresponding to the typical mesoporous structure of the materials. These results suggest that variation in nitrogen content does not strongly affect the mesopore structure of the samples. Their BJH pore size distributions are similar in the range of 10-20 nm (FIG. 1c). The physico-chemical properties of various samples are summarized in Table 1 and Table 2. The micropores created by the release of volatiles during the pyrolysis under inert gas flow are dependent on the melamine to phenol ratio. Increasing nitrogen incorporation in carbon framework causes inhibiting effect on the formation of micropores during pyrolysis, resulting in decreased micropore volume.

TABLE 1

Pore parameters and chemical nature of the NMCs.

| Sample | BET surface area ($m^2/g$) | Total pore volume[a] (cc/g) | Micropore volume[b] (cc/g) | Elemental analysis (wt %) | | | |
|---|---|---|---|---|---|---|---|
| | | | | C | N | H | O (cal.) |
| MC | 750 | 0.74 | 0.15 | 86.3 | 0 | 1.3 | 12.4 |
| NMC-1 | 836 | 1.08 | 0.12 | 80.4 | 5.1 | 1.0 | 13.5 |
| NMC-2 | 878 | 1.13 | 0.09 | 77.1 | 8.2 | 0.8 | 13.9 |
| NMC-3 | 844 | 1.09 | 0.07 | 73.0 | 11.6 | 0.7 | 14.7 |

[a]Total pore volume at $P/P_0 = 0.9$.
[b]Calculated by T-plot method.

TABLE 2

Physico-chemical properties of Ru-containing catalysts.

| Catalyst | Ru content[a] (wt %) | BET surface area ($m^2/g$) | Total pore volume[b] ($cm^3/g$) | Average Ru particle size[c] (nm) |
|---|---|---|---|---|
| 2 wt % Ru-MC | 1.92 | 722 | 0.71 | 6.1 |
| 2 wt % Ru-NMC-1 | 1.89 | 792 | 1.04 | 3.1 |
| 2 wt % Ru-NMC-2 | 1.91 | 849 | 1.10 | 2.5 |
| 2 wt % Ru-NMC-3 | 1.95 | 805 | 1.05 | 1.9 |
| 2 wt % Ru-AC | 1.81 | 991 | 0.51 | — |
| 2 wt % Ru-CeO$_2$ | 1.76 | 105 | 0.17 | — |
| 2 wt % Ru-MgO | 1.82 | 91 | 0.13 | — |
| 2 wt % Ru-Mg(Al)O | 1.79 | 130 | 0.22 | — |
| 2 wt % Ru-TiO$_2$ | 1.86 | 36 | 0.07 | — |
| 2 wt % Ru-γ-Al$_2$O$_3$ | 1.82 | 240 | 0.57 | — |

[a]Estimated by ICP-OES.
[b]Total pore volume at $P/P_0 = 0.9$.
[c]Calculated based on TEM analysis.

The formation of graphitic ordered carbon was further proved by Raman spectroscopy (FIG. 1d). Raman spectra show characteristic D- and G-bands of disordered graphitic carbon at 1335 and 1590 $cm^{-1}$ respectively. The D-band is a defects-induced Raman feature reflecting the non-perfect crystalline structure of the carbon, while G-band indicates the in-plane vibration of $sp^2$ carbon atoms. There is no dependence of the position of the two bands on the nitrogen content. The D-band appears to be stronger than G-band, suggesting amorphization of the graphitic carbon. The intensity ratios of the D-band to the G-band ($I_D/I_G$, calculated from integral area of the peaks) are 1.6, 1.8, 2.1 and 2.3 for MC, NMC-1, NMC-2 and NMC-3, respectively. These results show that the defects in graphite-like layers enhanced with increasing nitrogen content. The mesoporous structure of the MC and nitrogen-doped carbon samples can be further confirmed by transmission electron microscopy (TEM) observations (FIG. 2). From TEM images, nitrogen containing samples (FIGS. 2b,2c and 2d) have no differences when compared with their nitrogen-free counterpart (FIG. 2a), consisting of spherical mesopores with a disordered amorphous carbon structure. The Ru nanoparticle sizes as well as their distribution of various Ru containing catalysts were investigated by TEM (FIG. 3). It was found that Ru nanoparticles were dispersed unevenly and large agglomerated Ru nanoparticles were detected on the surface of MC with an average particle size of 6.1 nm (FIG. 3a,b). On the other hand Ru nanoparticles were dispersed homogeneously over nitrogen-doped carbons with an average particle size of 3.1, 2.5 and 1.9 nm for 2 wt % Ru-NMC-1, 2 wt % Ru-NMC-2 and 2 wt % Ru-NMC-3 catalyst, respectively (FIG. 3c,3d, 3e,3f,3g and 3h). Thus, it can be concluded that the dominant contributor for stabilizing Ru nanoparticles is the nitrogen doped in the carbon structure and increasing nitrogen content in the sample led to decrease in the size of Ru nanoparticles. X-ray photoelectron spectroscopy (XPS) was employed to investigate the nitrogen-carbon bonds formed in the carbon framework. In XPS only oxygen, carbon and nitrogen are detected in the overall region scanned (FIG. 4a). XPS of C 1s shows very similar peak at 284.6 eV, which is associated with the graphitic carbon, suggesting that most of the C atoms are assembled in conjugated honeycomb lattices. The N 1s spectra (FIG. 4b) are curve-fitted into three peaks with the binding energies at 398.2, 400.4 and 401.8 eV that correspond to pyridinic N (N1), pyrrolic N (N2) and graphitic N (N3), respectively. The peaks related to nitrogen bonded to oxygen (404-408 eV) are absent. It is important to note that the distribution of these nitrogen species is very similar at same pyrolysis temperature (800° C.), being independent of nitrogen content in the sample (FIG. 4c). As shown in FIG. 4c, regardless of nitrogen content, a majority of nitrogen atoms are localized at the edges of graphene sheets (N1 and N2) whereas small amount of nitrogen atoms are situated at the central region of graphene sheet (N3).

Example 5: Catalytic Activity in the Conversion of HMF to DMF a) Effect of Reaction Temperature Catalyst evaluation for hydrogenolysis of HMF to get DMF was performed using 2-propanol as a hydrogen donor in a batch reactor. FIG. 5 shows HMF conversion and product distributions as a function of reaction temperature over 2 wt % Ru-NMC-3 catalyst. The catalytic transfer hydrogenation (CTH) reaction occurs at a lower reaction temperature (80° C.) and DMF yield increased with increasing temperature. At lower temperature, the primary product was 2,5-bis(hydroxymethyl)furan (BHMF) and upon increasing the temperature to 160° C., BHMF is completely converted to DMF with a yield up to 84 mol % at 100 mol % HMF conversion after 8 h of reaction (Scheme 2). Other products observed at 120 and 140° C. are hydrogenated furans: 5-methyl furfural (MFU), 5-methyl furfuryl alcohol (MFA), 2-methylfuran (MF) and furfuryl alcohol (FA). The formation of FA indicates the occurrence of decarbonylation reaction, however, the yield of FA was low (<4 mol %). The formation of MFU suggested that hydrogenolysis of —OH group in HMF occur in parallel to the hydrogenation of the —CHO group. In addition, ethers are also observed at lower temperature (80 and 120° C.), which are formed via etherification of BHMF or MFA and 2-propanol. They are not observed upon increasing the reaction temperature (160 and 170° C.).

Scheme 1 General scheme for the catalytic transfer hydrogenation of (CTH) reaction for preparation of DMF and MF

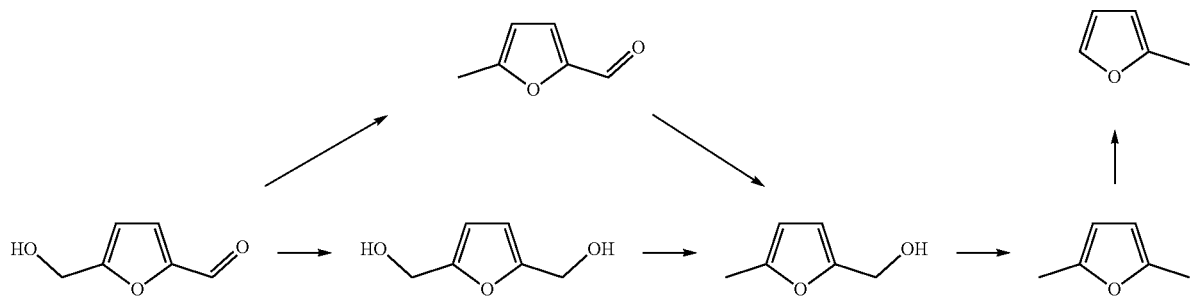

Scheme 2 Reaction network of the hydrogenolysis of HMF to DMF using 2-propanol and Ru—NMC catalyst.

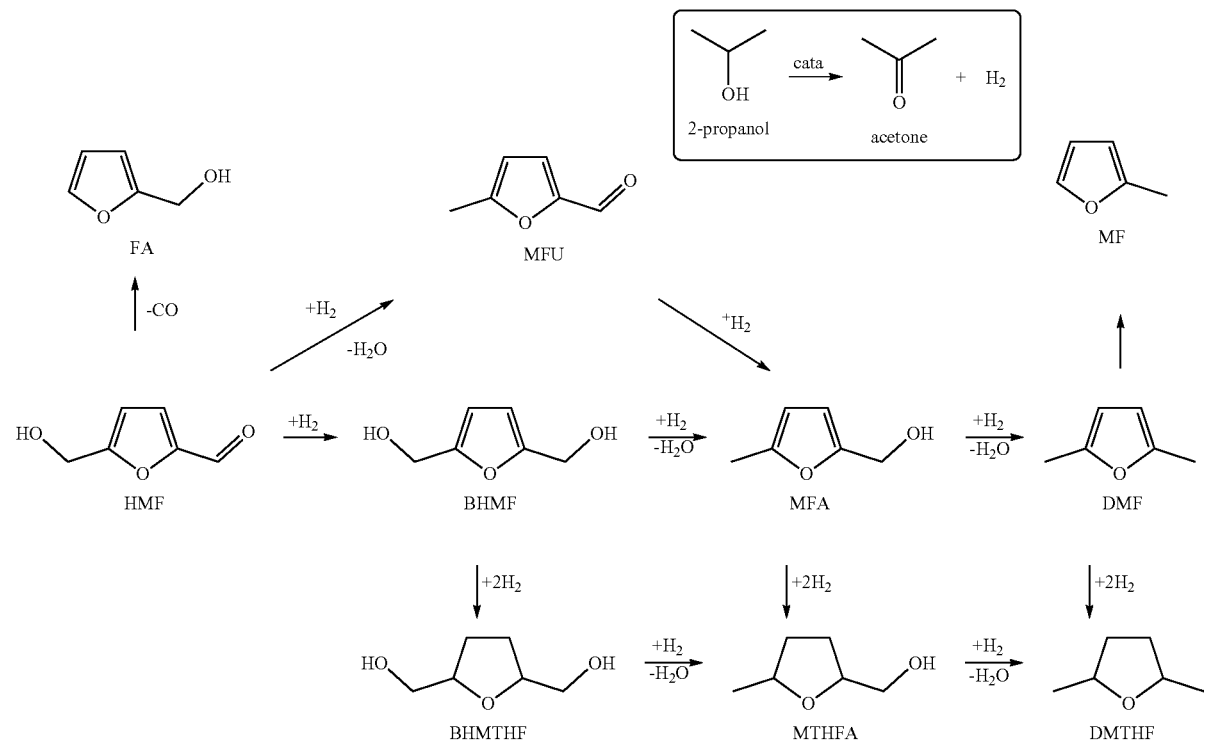

Compounds: 5-Hydroxymethylfurfural (HMF); 2,5-bis (hydroxymethyl)furan (BHMF); 5-methyl furfural (MFU); 5-methyl furfuryl alcohol (MFA); furfuryl alcohol (FA); 2,5-bis(hydroxymethyl)tetrahydrofuran (BHMTHF); 5-methyl tetrahydrofurfuryl alcohol (MTHFA); 2,5-dimethylfuran (DMF); 2,5-dimethyltetrahydrofuran (DMTHF); 2-methylfuran (MF).

b) Effect of Hydrogen Donors

The effect of hydrogen donor on HMF conversion and product yields was investigated at 160° C. over 2 wt % Ru-NMC-3. The results (FIG. 6) clearly indicate that the activity of catalyst heavily depends on the type of alcohol used. The HMF conversion increased from 40 to 100 mol % and the following reactivity order was observed: methanol<1-butanol<ethanol<1-propanol<2-butanol<2-propanol. Among the hydrogen donors tested, 2-propanol showed highest activity giving 84 mol % DMF yield. The formation of ethers was negligible in 2-propanol and 2-butanol but significant in other alcohols (2-14 mol %). This shows that etherification reaction favoured with lower chain alcohols (methanol, ethanol and 1-propanol) indicative of steric effect. These findings are in good agreement with the reported results, which show that for CTH, aliphatic secondary alcohols show better activity than aliphatic primary alcohols. The higher tendency to release hydrogen from secondary alcohols has been attributed to the highest reduction potential of corresponding dialkyl ketones.

c) Effect of Nitrogen Content in the Catalyst on CTH

In order to investigate the effect of nitrogen content of the catalyst on CTH activity, the Ru catalyst supported on various nitrogen containing mesoporous carbons and nitrogen-free carbon were tested for HMF hydrogenolysis (Table 3). The HMF conversions were 41, 61, 79 and 100 mol % with DMF yield of 11, 30, 55 and 84 mol % on 2 wt % Ru-MC, 2 wt % Ru-NMC-1, 2 wt % Ru-NMC-2 and 2 wt % Ru-NMC-3 catalysts, respectively. Therefore, it can be concluded that the catalytic activity is improved with increasing nitrogen content in the catalyst. The high catalytic performance of 2 wt % Ru-NMC-3 in HMF hydrogenolysis has been attributed to the uniqueness of the support-Ru interaction, i.e., N-doped mesoporous carbon-Ru heterojunction. The high nitrogen content in NMC-3 not only led to very stable and homogeneous dispersion of Ru nanoparticles but also enriches the electron density of the Ru nanoparticles, which accelerates the hydrogenolysis reaction, as compared to nitrogen-free catalyst (2 wt % Ru-MC). Moreover, 2 wt % Ru-NMC-3 catalyst is composed of small Ru nanoparticles (1.9 nm) that are surrounded by basic centers (nitrogen) provided by the support, which may favor ionic hydrogenation pathways and this is expected to be more active in hydrogenation reaction compared to non-ionic hydrogenation pathways. Sanchez-Delgado et al. reported heterolytic splitting of $H_2$ into $H^+$ and $H^-$ (ionic hydrogenation pathway) over Ru nanoparticles, assisted by the basic pyridinic groups of the support (poly(4-vinylpyridine)). During CTH reaction $H_2$ was produced and the $H_2$ partial pressure in the closed reactor has increased with the increasing N content of the catalyst. These results show that the nitrogen plays a key role in the dehydrogenation of 2-propanol leading to higher $H_2$ pressure. It is possible that adsorbed hydrogen species formed by the dehydrogenation of 2-propanol during CTH process can directly hydrogenate HMF molecule adsorbed on Ru nanoparticles instead of being released as $H_2$. To understand this prospect, HMF hydrogenation was performed at $H_2$ pressure of 7 bar (total pressure developed including $H_2$ partial pressure during CTH reaction at 160° C. over 2 wt % Ru-NMC-3 with 2-propanol) using tetrahydrofuran (THF) as solvent. The HMF conversion and DMF yields were 86 and 59 mol %, respectively, which were inferior to those using 2-propanol as hydrogen donor (compare entry 5 and 7 in Table 3). This result strongly suggests that HMF hydrogenation using hydrogen donors can be more efficient than that using external $H_2$ molecule. It is well known that there are differences between heterogeneous catalytic hydrogenation using hydrogen donor molecules as the source of hydrogen and hydrogenation using molecular $H_2$. The CTH reaction could occur through direct hydride transfer from 2-propanol to HMF.

TABLE 3

Product distributions for CTH of HMF of HMF over supported Ru catalysts.[a]

| Entry | Catalyst | HMF conv. (mol %) | Product yields (mol %) | | | | | TOF[e] (h$^{-1}$) |
| --- | --- | --- | --- | --- | --- | --- | --- | --- |
| | | | BHMF | MFA | DMF | DMTHF | Others[d] | |
| 1 | — | 8 | 0 | 0 | 0 | 0 | 8 | — |
| 2[b] | NMC-3 | 15 | 3 | 4 | 1 | 0 | 7 | — |
| 3 | 2 wt %Ru-NMC-1 | 61 | 7 | 22 | 30 | 0 | 2 | 7.5 |
| 4 | 2 wt %Ru-NMC-2 | 79 | 5 | 14 | 55 | 2 | 3 | 13.7 |
| 5 | 2 wt %Ru-NMC-3 | 100 | 0 | 0 | 84 | 8 | 8 | 21.0 |
| 6 | 2 wt %Ru-MC | 41 | 7 | 6 | 11 | 0 | 17 | 2.7 |
| 7[c] | 2 wt %Ru-NMC-3 | 86 | 1 | 3 | 59 | 13 | 10 | 14.7 |

[a]Reaction conditions: molar ratio of HMF to Ru (200); temperature (160 ° C.); $N_2$ pressure (20 bar); solvent and hydrogen donor (2-propanol, 25 mL); time (8 h).
[b]25 mg catalyst.
[c]7 bar $H_2$ pressure was used instead of 2-popanol and THF (25 mL) as solvent.
[d]It includes furfuryl alcohol (FA), 2-methylfuran (MF), ethers and some condensation compounds.
[e]TOF = turnover frequency (moles of DMF produced per mole of Ru per hour).

d) CTH of HMF Over Different Catalysts

The catalyst 2 wt % Ru-NMC-3 was compared with 2 wt % Ru-AC under the same reaction conditions as well as with other oxide-supported Ru nanoparticles, including 2 wt % Ru-CeO$_2$, 2 wt % Ru—MgO, 2 wt % Ru-TiO$_2$, 2 wt % Ru—Mg(Al)O and 2 wt % Ru-γ-Al$_2$O$_3$. Catalyst 2 wt % Ru-NMC-3 showed remarkably high activity in CTH, giving 100 mol % HMF conversion and 84 mol % DMF yield (Table 4). Oxide and AC supported Ru nanoparticles were not effective for this reaction, affording DMF in lower yields than 2 wt % Ru-NMC-3 catalyst. In case of 2 wt % Ru-γ-Al$_2$O$_3$ and 2 wt % Ru—TiO$_2$, the main product was BHMF (entry 6 and 7, Table 4). These results show that these two catalysts have ability towards carbonyl group hydrogenation to hydroxyl group, but have less ability for C—O bond hydrogenolysis. From these results, one could conclude that the nature of the support plays an important role in the activity and selectivity of Ru based catalysts in CTH reactions.

intermediate products such as BHMF and MFA formed in significant quantities, which are converted to DMF with prolonging the reaction time. On further increasing $H_2$ pressure (7 bar); the DMF yield reaches the maximum (68

TABLE 4

Product distributions for CTH of HMF over different catalysts.[a]

| Entry | Catalyst | HMF conv. (mol %) | Product yields (mol %) | | | | | TOF[c] (h$^{-1}$) |
|---|---|---|---|---|---|---|---|---|
| | | | BHMF | MFA | DMF | DMTHF | Others[b] | |
| 1 | 2 wt %Ru-NMC-3 | 100 | 0 | 0 | 84 | 8 | 8 | 21.0 |
| 2 | 2 wt %Ru-AC | 56 | 7 | 7 | 15 | 0 | 27 | 3.7 |
| 3 | 2 wt %Ru-CeO$_2$ | 39 | 10 | 9 | 6 | 0 | 14 | 1.5 |
| 4 | 2 wt %Ru-MgO | 37 | 10 | 4 | 6 | 0 | 17 | 1.5 |
| 5 | 2 wt %Ru-Mg(Al)O | 48 | 15 | 6 | 5 | 1 | 21 | 1.2 |
| 6 | 2 wt %Ru-TiO$_2$ | 45 | 26 | 1 | 0 | 0 | 18 | 0 |
| 7 | 2 wt %Ru-γ-Al$_2$O$_3$ | 60 | 35 | 2 | 0 | 0 | 23 | 0 |

[a]Reaction conditions: molar ratio of HMF to Ru (200); temperature (160 °C); $N_2$ pressure (20 bar); solvent and hydrogen donor (2-propanol, 25 mL); time (8 h).
[b]It includes ethers, FA, MF and some condensation compounds.
[c]TOF = turnover frequency (moles of DMF produced per mole of Ru per hour).

e) CTH of HMF Over Different Metal Catalysts

The CTH of HMF was investigated using NMC-3 supported Ru, Pt, Pd, Rh, Ni, Cu and Au catalysts. The HMF conversion varied in the range of 21 to 100 mol % and followed the reactivity order of Cu<Ni<Au<Rh<Pt<Pd=Ru (Table 5). Gratifyingly, an excellent DMF yield of 84 mol % with 100 mol % HMF conversion was obtained over Ru-based catalyst (Table 5, entry 1). Interestingly, when the reaction was conducted with Pd catalyst, significant amount of decarbonylation product, FA was obtained (Table 5, entry 3), indicating Pd is more suitable for HMF decarbonylation.

mol %) and the yield decreased on continuation of the reaction for further duration. This decreased in DMF yield is due to its ring hydrogenation, leading to the formation of DMTHF. On rising $H_2$ pressure further to 10 and 15 bar, has an adverse effect on the DMF yield. At higher $H_2$ pressure, DMF yield suppressed mostly due to the increased rate of consecutive ring hydrogenation of DMF, led to the formation of DMTHF in significant amounts. Moreover, the concentration of other undesirable by-products such as 5-methyl tetrahydrofurfuryl alcohol (MTHFA), 2,5-bis(hy-

TABLE 5

Product distributions for CTH of HMF over different metal catalysts.[a]

HMF → BHMF, MFA, FA, DMF, DMTHF, Others (Catalyst, $H_2$ donor)

| Entry | Catalyst | HMF conv. (mol %) | Product yields (mol %) | | | | | | TOF[c] (h$^{-1}$) |
|---|---|---|---|---|---|---|---|---|---|
| | | | BHMF | MFA | DMF | DMTHF | FA | Others[b] | |
| 1 | 2 wt % Ru-NMC-3 | 100 | 0 | 0 | 84 | 8 | 5 | 3 | 21.0 |
| 2 | 2 wt % Pt-NMC-3 | 75 | 5 | 8 | 31 | 2 | 1 | 28 | 7.7 |
| 3 | 2 wt % Pd-NMC-3 | 100 | 0 | 5 | 15 | 0 | 62 | 18 | 3.7 |
| 4 | 2 wt % Rh-NMC-3 | 66 | 25 | 15 | 11 | 4 | 1 | 10 | 2.7 |
| 5 | 2 wt % Au-NMC-3 | 40 | 25 | 3 | 2 | 0 | 2 | 8 | 0.5 |
| 6 | 5 wt % Ni-NMC-3 | 25 | 6 | 1 | 3 | 0 | 1 | 14 | 0.7 |
| 7 | 5 wt % Cu-NMC-3 | 21 | 3 | 3 | 2 | 0 | 2 | 11 | 0.5 |

[a]Reaction conditions: molar ratio of HMF to metal (200); temperature (160° C.); $N_2$ pressure (20 bar); solvent and hydrogen donor (2-propanol, 25 mL); time (8 h).
[b]It includes ethers, MF, 5-methyltetrahydrofurfuryl alcohol (MTHFA) and some condensation products.
[c]TOF = turnover frequency (moles of DMF produced per mole of metal per hour).

f) Catalytic Activity for the Conversion of HMF to DMF Using $H_2$

The effect of $H_2$ pressure on the DMF yields was studied by varying the pressure from 2-15 bar at 160° C. in THF solvent over 2 wt % Ru-NMC-3 catalyst (FIG. 7). When the reaction was carried out at low pressure (2 and 5 bar), the droxymethyl)tetrahydrofuran (BHMTHF) and hexanediol increased at higher $H_2$ pressure.

g) Recyclability Study

The recyclability of the 2 wt % Ru-NMC-3 catalyst was evaluated by repeating the reaction with the same catalyst (FIG. 8). The results show that the catalytic performance remains same even after being reused for four times. These results indicate good stability of the catalyst. ICP-OES analysis showed no leaching of Ru after each recycle. Moreover, the amount of Ru in the catalyst after four cycles was found to be similar to that of starting catalyst.

Example 6: Catalytic Activity for the Conversion of Furfural to MF a) Effect of Reaction Temperature The effect of temperature on the furfural conversion and product yields over 2 wt % Ru-NMC-3 catalyst was investigated by varying the reaction temperature in the range of 50-140° C. (FIG. 9). The primary product of the transfer hydrogenation of furfural was FA, which is prominent at lower temperature (80, 100 and 125° C.). In a consecutive step, hydrogenolysis of the —OH group in FA yields MF up to 87 mol % with 100 mol % furfural conversion at 140° C. In parallel to hydrogenation, furfural also undergoes decarbonylation reaction to furan. Furthermore, furan-ring hydrogenated products like 2-methyl tetrahydrofuran (MTHF) and tetrahydrofurfuryl alcohol (THFA) have also been observed.

b) Effect of Hydrogen Donors

The effect of hydrogen donor on furfural conversion and product yields was investigated at 140° C. over 2 wt % Ru-NMC-3 catalyst (FIG. 10). The results clearly suggested that the catalyst activity is greatly depends on the nature of hydrogen donor. The furfural conversion increased from 44 to 100 mol % and follows the reactivity order: methanol<1-butanol<ethanol<1-propanol<2-butanol<2-propanol.

Among the hydrogen donors tested, 2-propanol displayed the highest activity leading to 87 mol % MF yield with 100 mol % furfural conversion. These results are in good agreement with the reported results, which normally reports that in CTH secondary alcohols have a better tendency to release hydrogen than primary alcohols.

Advantages of invention:
1. Simple and environment friendly process
2. The novel transition metal catalyst, especially Ru based catalyst exhibits excellent activity for the CTH of biomass-derived HMF and furfural.
3. This catalyst also exhibited good recyclability and can be reused many times without loss in activity.
4. The CTH process using the catalyst does not require molecular hydrogen as hydrogen source. It uses alcohol organic acid, organic acid salts as hydrogen source.
5. The process does not require use of any co-catalysts.

We claim:

1. A catalyst comprising:
   a transition metal supported on nitrogen doped mesoporous carbon,
   wherein the transition metal(s) either alone or in combination is from 0.5 weight % to 5 weight % of the catalyst; and wherein average particle/crystal size of the transition metal (s) is from 1 nm to 5 nm; and wherein the nitrogen content is from 8.2 weight % to 15 weight % of the catalyst.

2. The catalyst of claim 1, wherein the transition metal is selected from the group consisting of Ru, Pt, Pd, Rh, Au, Ag, Os, Ir, Cu, Ni, Re, Cr, Mn, Fe, Zn, Co, and combinations of any two or more of the transition metals.

3. The catalyst of claim 1, wherein a BET surface area of the transition metal(s) catalyst is from 30 $m^2/g$ to 1200 $m^2/g$.

4. The catalyst of claim 3, wherein the BET surface area of the transition metal(s) catalyst is from 36 $m^2/g$ to 1200 $m^2/g$.

5. The catalyst of claim 1, wherein total pore volume of the transition metal(s) catalyst is from 0.07 $cm^3/g$ to 1.2 $cm^3/g$.

6. A process for synthesis of the catalyst according to claim 1, the process comprising:
   (a) dispersing nitrogen doped mesoporous carbon in deionized water under ultrasonication to obtain a dispersion;
   (b) charging transition metal chloride to the dispersion obtained in (a) under ultrasonication and stirring the dispersion at 70° C. to 90° C. for 6 hours to 12 hours to obtain a mixture;
   (c) cooling the mixture of (b) and charging aqueous solution of $NaBH_4$ under ultrasonication and stirring for 30 minutes to 60 minutes to obtain a catalyst mixture; and
   (d) filtering the catalyst mixture obtained in (c) and washed with deionized water and dried at 80° C. to 100° C. for 10 hours to 12 hours to obtain the catalyst.

7. The process of claim 6, wherein the transition metal chloride is selected from the group consisting of chlorides of Ru, chlorides of Pt, chlorides of Pd, chlorides of Rh, chlorides of Au, chlorides of Ag, chlorides of Os, chlorides of Ir, chlorides of Cu, chlorides of Ni, chlorides of Re, chlorides of Cr, chlorides of Mn, chlorides of Fe, chlorides of Zn, chlorides of Co, and combinations of any two or more of the transition metal chlorides.

8. A process for the synthesis of 2,5-Dimethylfuran (DMF) or 2-Methylfuran (MF) using the catalyst according to claim 1, the process comprising:
   stirring 5-hydroxymethylfurfural (HMF) and the catalyst, or furfural and the catalyst, in the presence of a catalytic transfer hydrogenation (CTH) agent at a temperature from 80° C. to 170° C. for a period 0.5 hours to 10 hours, to convert the HMF to DMF or to convert the furfural to MF.

9. The process of claim 8, wherein the CTH agent is selected from the group consisting of alcohols, organic acids, and mixtures thereof.

10. The process of claim 9, wherein the alcohol is selected from the group consisting of 2-propanol, 2-butanol, methanol, ethanol, and 1-propanol.

11. The process of claim 9, wherein organic acid is selected from the group consisting formic acid, acetic acid, propionic acid, and butyric acid.

12. The process of claim 8, wherein said process is carried out in the presence of molecular hydrogen and the catalytic transfer hydrogenation agent.

13. The process of claim 8, wherein HMF and the catalyst are stirred in the presence of the CTH agent and the HMF is converted to DMF; wherein a yield of DMF is greater than 81%; and wherein a conversion of HMF is 100%.

14. The process of claim 9, wherein transition metal(s) content either alone or in combination in said catalyst is from 1 weight % to 5 weight %.

15. The catalyst of claim 1, wherein a BET surface area of the transition metal(s) catalyst is from 805 $m^2/g$ to 1200 $m^2/g$, and wherein total pore volume of the transition metal(s) catalyst is from 1.05 $cm^3/g$ to 1.2 $cm^3/g$.

* * * * *